(12) United States Patent
Meier et al.

(10) Patent No.: US 9,396,291 B2
(45) Date of Patent: Jul. 19, 2016

(54) COMPUTER-IMPLEMENTED METHOD FOR DIGITALLY DESIGNING A DENTAL RESTORATION AND A COMPUTER-READABLE MEDIUM

(75) Inventors: Marcus Meier, Basel (CH); Martin Manzer, Berlin (DE); Uwe Lawitschka, Berlin (DE); Melanie Welge, Gräfelfing (DE)

(73) Assignee: Straumann Holding AG, Basel (CH)

( * ) Notice: Subject to any disclaimer, the term of this patent is extended or adjusted under 35 U.S.C. 154(b) by 497 days.

(21) Appl. No.: 13/812,061

(22) PCT Filed: Aug. 23, 2011

(86) PCT No.: PCT/EP2011/004230
§ 371 (c)(1),
(2), (4) Date: Mar. 29, 2013

(87) PCT Pub. No.: WO2012/028270
PCT Pub. Date: Mar. 8, 2012

(65) Prior Publication Data
US 2013/0179126 A1    Jul. 11, 2013

(30) Foreign Application Priority Data

| Aug. 31, 2010 | (EP) | 10009046 |
| Aug. 31, 2010 | (EP) | 10009047 |
| Mar. 18, 2011 | (EP) | 11002250 |

(51) Int. Cl.
G06F 17/50    (2006.01)
A61C 13/00    (2006.01)
A61C 5/10    (2006.01)

(52) U.S. Cl.
CPC . *G06F 17/50* (2013.01); *A61C 5/10* (2013.01); *A61C 13/0004* (2013.01)

(58) Field of Classification Search
CPC ............ A61C 13/0004; G06F 17/50
USPC .............. 703/1; 433/24; 700/98, 118
See application file for complete search history.

(56) References Cited

U.S. PATENT DOCUMENTS

2009/0246726 A1    10/2009    Chelnokov et al.

OTHER PUBLICATIONS

Stoll et al., "A Volumetric Approach to Interactive Shape Editing", Jun. 2007, MPI-I-2007-4-004, pp. 1-23.*

(Continued)

*Primary Examiner* — Kamini S Shah
*Assistant Examiner* — Juan Ochoa
(74) *Attorney, Agent, or Firm* — Therese Hendricks, Esq.

(57) ABSTRACT

Computer-implemented method for digitally designing a dental restoration for a rest tooth, wherein the rest tooth is described by data of the rest tooth and wherein a tooth template is described by data of the tooth template, the method comprising automatically deforming the tooth template by means of Laplacian surface deformation such that a prepared part of the rest tooth is covered by a portion of the tooth template, wherein the Laplacian surface deformation comprises automatically generating a line which is going through a point, such as a vertex or a point inside a polygonal of a mesh, on the surface of the rest tooth or the tooth template and which is directed along the normal direction at said point; when the line intersects with the tooth template and with the surface of the rest tooth, automatically choosing the intersection point of the line with the tooth template as handle and the intersection point with the surface of the rest tooth as target; and automatically deforming the tooth template. Further, the invention is related to a computer-readable medium having stored thereon instructions, which when executed by a processor, are adapted to perform the method steps of the inventive computer-implemented method.

17 Claims, 4 Drawing Sheets

(56) References Cited

OTHER PUBLICATIONS

Tao et al., "Computer Aided Design and Deformation of the Complete Crown", May 16-18, 2008, The 2nd International Conference on Bioinformatics and Biomedical Engineering ICBBE, pp. 1699-1702.*

Tao et al., "Digital Design of Fixed Bridge Framework", May 16-18, 2008, 2nd International Conference on Bioinformatics and Biomedical Engineering, ICBBE, pp. 1792-1795.*

3.1 Tangent plane and surface normal—MIT, Dec. 2009, pp. 1-4.*

Yuan et al., "Single-tooth modeling for 3D dental model", 2010, International Journal of Biomedical Imaging vol. 2010, Article ID 535329, pp. 1-14.*

Au et al., "Dual laplacian editing for meshes", May/Jun. 2006, IEEE Transactions on Visualization & Computer Graphics, vol. 12, No. 3, pp. 386-395.*

International Preliminary Report on Patentability dated Mar. 14, 2013 in corresponding PCT/EP2011/004230.

"Dental Inlay and Onlay Construction by Iterative Laplacian Surface Editing" by Tillmann Steinbrecher and Maik Gerth, Fraunhofer IGD, Germany, Eurographics Symposium on Geometry Processing 2008 Pierre Alliez and Szymon Rusinkiewicz (Guest Editors), vol. 27 (2008), No. 5, pp. 1441-1447.

Steinbrecher T. "Dental Inlay and Onlay Construction by Iterative Laplacian Surface Editing", Computer Graphics Forum Jul. 2008, Blackwell Publishing LTD GB, Eurographics Symposium on Geometry Processing 2008, Pierre Alliez and Szymon Rusinkiewicz, vol. 27 (2008), No. 5, pp. 1441-1447.

European Search Report mailed Jan. 13, 2011 in application EP 10 00 9046.

European Search Report mailed Mar. 24, 2011 in application EP 10 00 9047.

European Search Report mailed Dec. 2, 2011 in application EP 11 00 2250.

European Search Report mailed Aug. 29, 2012 in application EP 12 00 1137.

International Search Report mailed Dec. 12, 2011 in PCT/EP2011/004232.

International Search Report mailed May 3, 2012 in PCT/EP2011/004230.

International Search Report mailed Feb. 13, 2012 in PCT/EP2011/004231.

* cited by examiner

COMPUTER-IMPLEMENTED METHOD FOR DIGITALLY DESIGNING A DENTAL RESTORATION AND A COMPUTER-READABLE MEDIUM

FIELD OF THE INVENTION

The invention relates to a computer-implemented method for digitally designing a dental restoration and to a computer-readable medium.

BACKGROUND

The design of tooth restorations requires a deep dental knowledge. The challenge of computer aided tooth design lies in the computation of a functional correct morphology of the missing chewing surface. A solution must be robust and automated such that the user actually benefits from time saving and better results.

The article "Dental inlay and onlay construction by iterative Laplacian surface editing" by T. Steinbrecher et al. (Eurographics Symposium on Geometry Processing 2008; Jul. 2-4, 2008 in Copenhagen, Denmark; Volume 27(2008), No. 5; p. 1441-1447) discloses that a model tooth may be adapted by using Laplacian surface editing to a patient's tooth. After adaptation, the part of the model tooth lying above the cavity will be joined with the cavity mesh to create the actual inlay reconstruction. The part of the model tooth lying above the healthy part of the tooth should be adapted to the remaining tooth surface. The model tooth is segmented into parts that lie "above cavity" or "on surface".

From each vertex of the model tooth that is not yet clarified as "above cavity", two rays are cast, one towards the centre of the tooth to be reconstructed, and one away from it. Thereby all rays by definition pass through the centre of the tooth to be reconstructed. Only the closest hit point is considered. The hit points are then classified according to their location as "above cavity", "on surface", or "undefined".

The adaptation is an iterative process, alternating segmentation and deformation. For vertices classified as "on surface", ray collisions with the tooth to be reconstructed are used again.

As the rays are cast starting from a vertex of the model tooth for each iteration also the segmentation has to be performed again. This is because by starting from a vertex of the model tooth, it is unknown where the location of a hit point on the tooth to be reconstructed will be. Even before the first deformation of the model tooth it needs to be segmented.

After the adaptation is completed, all vertices classified as "on surface" and not having a neighbour that is classified as "above cavity" will be removed and thus a mesh that covers the cavity remains wherein its boundary is aligned to the preparation margin.

SUMMARY OF THE INVENTION

It is the object of the present invention to enable an automatic design of dental restorations by means of Laplacian surface deformation resulting in stable and reliable data for a dental restoration.

All the method steps described in the following may be performed automatically and do not necessarily need the interaction of a user.

The present invention relates to a computer-implemented method for digitally designing a dental restoration, such as a inlay, onlay, veneer, or partial crown or the like, for a rest tooth, wherein the rest tooth is described by data of the rest tooth and wherein a tooth template is described by data of the tooth template, wherein the method comprises the step of automatically deforming the tooth template by means of Laplacian surface deformation such that a prepared part of the rest tooth is covered (matched) by a portion of the tooth template, wherein the Laplacian surface deformation comprises automatically generating a line which is going through a point, such as a vertex or a point inside a polygonal of a mesh, on the surface of the rest tooth or the tooth template and which is directed along the normal direction at said point and when the line intersects with the tooth template and with the surface of the rest tooth, automatically choosing the intersection point of the line with the tooth template as handle and the intersection point with the surface of the rest tooth as target and automatically deforming the tooth template.

A normal direction to a surface at a point is typically the same as the normal direction to the tangent plane to said surface at said point.

A rest tooth may be considered as a tooth of a patient and/or (digital) data describing it, wherein said tooth is not complete, i.e. has missing parts, due to caries, dental preparation like milling and so on. For the processes in the computer-implemented method digital data of the rest tooth may be used, wherein these data may be achieved by scanning of a dental model of the rest tooth or by directly scanning the patient's rest tooth. The surface of the rest tooth may be described by a mesh of triangles, wherein the triangles may all be the same or wherein the triangles may have different shapes. It is also possible to use other polygons and/or use different polygons (e.g. like triangles and pentagons) in one mesh.

The rest tooth may have a prepared surface/prepared part which in general means that this surface/part has been prepared, e.g. by a dentist by milling. Preferably, the prepared surface/part may be provided with a dental restoration. Further, the rest tooth may have an unprepared surface/unprepared part at which the intact surface of the rest tooth is present. In some cases a non-intact surface of the rest tooth may be considered as "unprepared", e.g. in case no dental restoration should or will be provided to this surface of the rest tooth.

A tooth template may represent a digital representation of a generic tooth, wherein tooth templates according to the different tooth types (molar, premolar, incisor etc.) may be provided. The surface of the tooth template may be described by a mesh of triangles, wherein the triangles may all be the same or wherein the triangles may have different shapes. It is also possible to use other polygons and/or use different polygons (e.g. like triangles and pentagons) in one mesh.

The data of the tooth template may comprise a polygonal mesh describing the surface of the tooth template and the Laplacian surface deformation may further comprise using a handle that lies inside a polygon of the mesh of the tooth template.

The normal direction of a point within a triangle may be defined as the normal of that triangle or an average of the normal of this triangle and neighbouring triangles. A normal direction at a vertex (corner of a triangle) can be defined by the average of the normal directions of the triangles that have this vertex as a corner point or of triangles that lie within a sphere or volume of a predefined size (and/or shape) around the vertex. The average may be a weighted average wherein the weight may depend on the size of a triangle or it may be an unweighted average where all triangles considered for averaging are taken into account with equal weights.

Moreover, automatically deforming the tooth template in the Laplacian surface deformation may further comprise moving the handle towards the target.

It has been found that by using a handle that lies in a direction normal to the surface at the point of the target or a target that lies in a direction normal to the surface at the point of the handle yields very robust and reliable results using the Laplace surface deformation. By having handles and targets aligned in a direction normal either to the surface of the rest tooth or normal to the surface of the tooth template a surprisingly good choice of a handle and a corresponding target is found which allows for deformation of a template into a proper tooth surface.

It turns out to be of advantage to firstly define a target on the surface of the rest tooth and then to identify the corresponding handle in a direction normal to the surface of the rest tooth for various reasons. It can be assured that a target is provided at specific points of the surface of the rest tooth which are of particular interest. Such a point may e.g. be on the preparation margin. By firstly choosing the target on the surface of the rest tooth and then a corresponding handle it can be assured that a point of particular importance is taken into account for the surface deformation. If first the handles are defined and afterwards the corresponding targets are chosen, then it can not be assured that specific points of the surface of the rest tooth which are of particular interest are is taken into account. The preparation margin defines the border line of the prepared surface and the unprepared surface of the rest tooth that should be provided with a dental restoration. Taking points of the preparation margin into account for the surface deformation results in a smooth transition at the preparation margin, i.e. a smooth transition between the dental restoration and the rest tooth at the preparation margin.

For the targets and for the handles any point of a surface can be used. This means that a point on a surface of the rest tooth or a point on the template can be either a point inside a triangle (or polygon in general) or may be a corner of a triangle (or polygon in general) in case the surface of the rest tooth and the template are described by a mesh comprising triangles (or polygons in general). This on the one hand gives more flexibility in the choice of targets and handles as compared to the prior art but additionally allows for triangles (or polygons in general) of largely different sizes to be used. There is no need to have a large number of relatively small triangles in order to describe the surface of the rest tooth or the tooth template which assures that there is a sufficiently high density of vertices in order to perform a reasonable surface deformation. Since in the present method also points inside a triangle may be used there is no need for a large number of vertices and triangles of largely different size may be used. E.g. triangles having a two dimensional size of their surface 10 times or 50 times the two dimensional size of the surface of the smallest triangle of the data set can be used. This allows for reduced data sets for the digital description of the surface of the rest tooth and of the template in comparison to the prior art.

All vertices of a portion of a mesh describing the rest tooth portion that is considered for the Laplacian deformation can be used as targets or only a portion (subset thereof). Also at least one point of each triangle (polygon) of a mesh describing the rest tooth portion that is considered for the Laplacian deformation can be used as targets or only a portion (subset) of the triangles.

The Laplacian surface deformation may further comprise iteratively performing the deformation of the tooth template.

By having the targets defined on the surface of the rest tooth the handles can be identified without significant computational effort between two iterations. In particular there is no need for a new separate segmentation of the template as in the prior art since the targets, which are used for defining the position of handles do not necessarily change from one iteration to another. In the cited prior art after each iteration a new segmentation has to be carried out which is computationally very expensive.

Iteratively performing the deformation of the tooth template may use a handle weight that is increased as the iteration process proceeds, preferably starting with a pre-defined minimum handle weight.

By iteratively increasing the weight, the general position of the tooth template may be first adjusted to the outer surface of the rest tooth, thus the shape preservation may be predominant and self-intersection may be avoided. As the iteration proceeds and weights increase, the method may find correct handles and the template may be more and more deformed towards the surface of the rest tooth.

The method may further comprise the step of defining the handle weight for the deformation step as a product comprising a global weight increasing with each iteration step, and at least one or two of a distance weight decreasing with increasing distances between the target and the handle, wherein the dependence of the distance weight on the distance may vary with each iteration step, or an angle weight that depends on the angle between the normal direction of the target and the normal direction of the handle.

The global weight may increase with the iteration process and may deform the tooth template more and more. To further penalize false handle selections both distance and normal derivation between the target and the handle may be taken into account.

In order to allow for a general position of the template, weights may be independent from the distance at the beginning of the iteration process. As the iteration proceeds large distances may be penalized more and more by reducing the respective handle weights. This may reduce the impact of false projections. The less the distance, the more certain it may be that a correct projection is found.

A result of the inventive method may be that the transition between the rest tooth and the tooth template is as smooth as possible, which means that sharp edges and transitions which may achieve high loads are prevented.

The method may further comprise the step of automatically extracting a portion of the tooth template by digitally cutting the deformed tooth template along a preparation margin.

For designing the dental restoration, it may be sufficient to use the deformed tooth template that is located within the preparation margin as this is the area that should be provided with the dental restoration in order to achieve a complete tooth structure.

Moreover, the method may comprise the step of combining data representing the cut out deformed tooth template portion with data representing the surface of the rest tooth inside the preparation margin to provide a three-dimensional design of the dental restoration.

The surface of the rest tooth may have been scanned in order to get a corresponding data set. The rest tooth may comprise prepared regions, i.e. regions where original tooth material is missing either by medical defects and/or milling. The preparation margin defines the border line between prepared regions of the rest tooth and regions in which the rest tooth has its original shape. Thus, for the definition and thus also for the design of a complete dental restoration both the cut out deformed tooth template and the surface of the rest tooth inside the preparation margin have to be known in order to define and thus may be able to design the shape of the dental restoration.

Further, a cement gap and/or a spacer gap may be added to the data representing the surface of the dental restoration that would be in contact with or facing towards the rest tooth, the so-called lower surface.

The cement gap may be filled with dental cement or the like in order to fix a physical dental restoration to a rest tooth of a patient. This gap may be provided between the dental restoration and the surface of the rest tooth by providing a dental restoration with dimensions smaller than the space available at the rest tooth. The thickness of the cement gap may be between 10 and 60 µm, or may be smaller or thicker, e.g. depending on the grain size of the dental cement and/or the thickness of the dental restoration.

The spacer gap may be provided in addition to the cement gap (or alone), e.g. to provide a broadening of the cement gap at positions away from the preparation margin, e.g. to increase the amount of cement that may be used for fixing the dental restoration.

The adding may be performed by applying an offset along the normal directions of points on the lower surface, such as vertices, wherein preferably the normal directions may be averaged about a defined region around each point.

A cement gap may be required to provide space for the cement that is needed to securely attach a physical dental restoration to a rest tooth of a patient. An additional spacer gap may be provided. Next to the preparation margin only the cement gap may be provided and at a first predefined distance to the preparation margin a smooth transition from the cement gap to the spacer gap may be provided, reaching some predefined spacer gap thickness at a second predefined distance from the preparation margin.

The surface of the dental restoration may be further adapted according to a cutter radius (e.g. of a milling tool) that will be used for preparing the physical dental restoration.

An adaptation to the cutter radius may be needed to ensure that the manufactured dental restoration fits to the rest tooth and to ensure that the dental restoration may be manufactured with all its required details. For example, when the cutter radius has a dimension that is larger than a structure that the dental restoration to be manufactured should have this structure would have to be adapted, i.e. the structure must be designed to have a size corresponding to the cutter radius.

The method may further comprise the step of determining whether the dental restoration has a pre-defined minimum thickness, wherein the minimum pre-defined thickness may have different or equal values in different regions of the dental restoration, preferably by determining whether the vertices of the cut out deformed tooth template have a predetermined distance to the lower surface, wherein the pre-defined distance may have different or equal values in different regions of the dental restoration.

One possibility to determine whether the dental restoration would have a pre-defined minimum thickness is defining a volume on the prepared part of the rest tooth, the surface of the volume not being in contact with the prepared part of the rest tooth and describing a so-called minimal surface which may define the minimum wall thickness the dental restoration may have.

The method may further comprise the step of moving vertices of the cut out deformed tooth template that lie inside the volume to the surface of the volume not being in contact with the prepared part of the rest tooth by means of the Laplacian surface deformation.

For a computer-aided manufacturing of the dental restoration or any other manufacturing process the dental restoration may have to have a predefined minimal wall thickness to ensure that the dental restoration will not break or will not be damaged in some way during the manufacturing process and/or when being attached to a rest tooth and/or to during daily use in the attached state.

For this Laplacian surface deformation (to ensure a minimal thickness), a handle weight may be defined wherein no iteration depending weight is needed as no general positioning is required in case of adapting the dental restoration to provide a minimum wall thickness.

During this Laplacian surface deformation, first the deformation may be applied to the boundary of the deformed tooth template while fixing handles in the interior of the deformed tooth template, and then in a second step the deformation may be applied to the interior while fixing handles on the boundary. The boundary of the deformed tooth template may be defined by the circumferential border of the surface.

These two subsequent processes ensure that the Laplacian surface deformation does not only move the deformed tooth template out of the minimal surface but deforms it such that is located out of the minimal surface.

The method may further comprise the step of positioning the tooth template, which preferably may be selected from a data base comprising one or more tooth templates for one or more tooth types, with respect to rest tooth by aligning the rest tooth and the tooth template to coincide in x direction and in z direction.

Both the coordinate systems of the rest tooth and the tooth template may have the x direction in buccal (vestibular) direction, the y direction along the mesial-distal axis and the z direction in occlusal direction.

The position of the tooth template may be adjusted to a maximum z value that may be defined by a highest extend of one or more neighbouring teeth. A plane may be drafted perpendicular to the occlusal axis of said rest tooth and its maximum value of height of the rest tooth of any of the neighbouring tooth. Then the tooth template may be adjusted such that it has at least one common point with this plane but does not intersect the plane. In case no neighbouring tooth or teeth is or are present the plane may be provided at a z value which may be offset by predefined value from the top value of the rest tooth.

Moreover, the tooth template may be scaled to x and y direction according to the horizontal extent of the prepared surface of the rest tooth, wherein preferably no scaling in z direction is performed.

Due to the local coordinate systems of rest tooth and tooth template, the translation of the tooth template to adjust it to a defined height and the scaling in buccal direction, an automated positioning of the tooth template (prior to the Laplace surface deformation) may be achieved.

A further aspect is given by a computer-implemented method for digitally designing a dental restoration for a rest tooth, wherein the rest tooth is described by data of the rest tooth and wherein a tooth template is described by data of the tooth template, the method comprising the step of automatically deforming the tooth template by means of Laplacian surface deformation such that a prepared part of the rest tooth is covered (matched) by a portion of the tooth template wherein the data describing the tooth template define a mesh comprising polygons, such as triangles and one or more handles for the Laplacian surface deformation are provided inside of the polygon.

By having one or more handle provided inside of a polygon, such as a triangle, there is no need for a dense set of small triangles as explained above.

According to another aspect there is provided a computer-implemented method for digitally designing a dental restoration for a rest tooth, wherein the rest tooth is described by data of the rest tooth and wherein a tooth template is described by data of the tooth template, the method comprising the step of automatically deforming the tooth template by means of Laplacian surface deformation such that a prepared part of the rest tooth is covered by a portion of the tooth template wherein firstly a point on the surface of the rest tooth is chosen as a target of the Laplacian surface deformation and then based on the chosen target a point on the tooth template is chosen as a handle.

Thereby firstly it can be assured that specific points such as points on the preparation margin are used for defining a target (as explained above) and secondly no renewed segmentation of the template is necessary as the target points do not change from iteration to iteration.

In a further aspect there is provided a computer-implemented method for digitally modifying a dental restoration for a rest tooth, wherein the dental restoration is described by data of the dental restoration, the method comprising the step of:

automatically deforming the dental restoration by means of Laplacian surface deformation such that the thickness thereof is increased up to a predefined minimum thickness of the dental restoration.

Thereby it is made sure that the dental restoration has a minimum thickness, which makes sure that the dental restoration can be manufactured without significant problems and also makes sure that the dental restoration does not break in use due to a to small thickness. At the same time the digital deformation of the dental restoration by the Laplacian surface deformation leads to smooth surfaces without kinks or sharp bends. Details of this Laplacian surface deformation are disclosed above in and in relation to FIG. 6.

Further, the present invention is related to a computer-readable medium having stored thereon instructions, which when executed by a processor, are adapted to perform any of the above identified method steps.

BRIEF DESCRIPTION OF THE DRAWINGS

Preferred embodiments of the invention will be illustrated with reference to the enclosed figures. In the figures.

DETAILED DESCRIPTION

The schematic representations shown in FIGS. 1 to 6 may be displayed for example on a computer display or the like, wherein data sets may be provided corresponding to the depicted objects.

Figure 1:
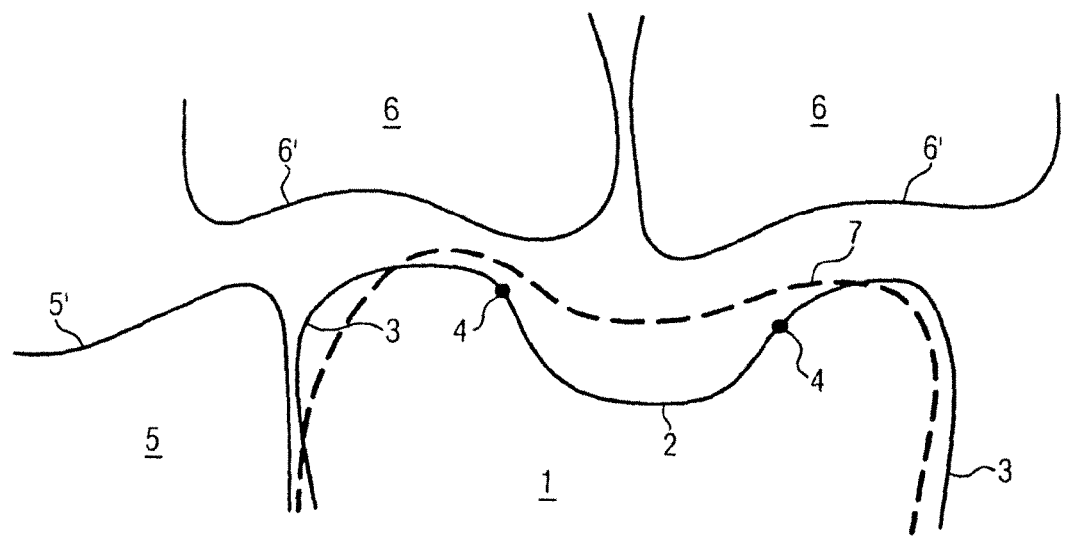
FIG. 1 shows a prepared tooth with surrounding teeth and a tooth template.

FIG. 1 shows schematically a rest tooth 1 comprising a prepared region, the so-called lower surface 2, which is separated from the unprepared rest tooth, the so-called outer surface 3, by the preparation margin 4. The depicted rest tooth 1 has a neighbouring tooth 5 with an approximal surface 5' and two opposite teeth 6 with occlusal surfaces 6'. In order to provide the rest tooth 1 with a dental restoration a tooth template 7 may be used. The tooth template 7 may be positioned with respect to the rest tooth 1 such that the local coordinate systems of the rest tooth 1 and the tooth template 7 coincide in x direction and in z direction. For example, the x direction may be given by the buccal direction, the y direction by the mesial-distal axis and the z direction by the occlusal direction.

The rest tooth 1 shown in FIG. 1 comprises a cavity as prepared region, which means that the dental restoration to be designed may be an inlay. However, a rest tooth may also have prepared regions extending on surface regions, such as one or more cusp tips, which means that the dental restoration to be designed may be an onlay or partial crown. A veneer may have to be designed when a thin layer of the tooth surface has to be provided with a dental restoration.

Figure 2:
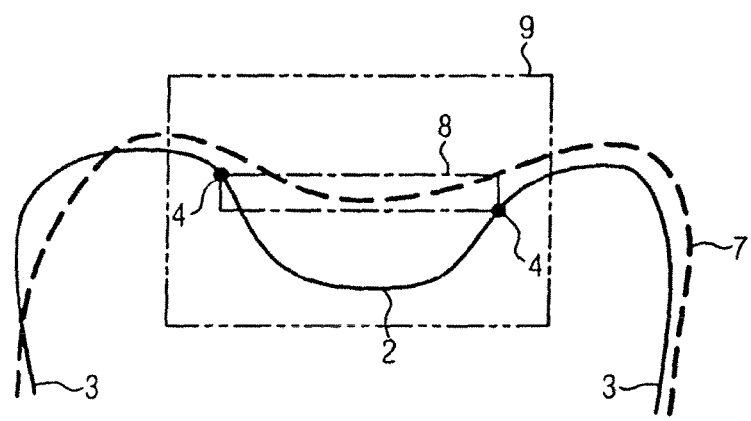
FIG. 2 shows a prepared tooth, a tooth template, first and second bounding boxes.

As shown in FIG. 2, for performing the deformation of the tooth template 7 a first bounding box 8 may be defined by the preparation margin 4. A second bounding box 9 may be defined in a predefined distance from the first bounding box 8 such that part of the tooth template 7 and part of the outer surface 3 of the rest tooth 1 are cut out. By using the second bounding box 9 the deformation process may be simplified and accelerated as not the whole tooth template 7 will be deformed but only the part of it which is located within the second bounding box 9. A predefined distance to the first bounding box 8 may be kept in order to avoid cut out fissures in the tooth template 7. However, for performing the deformation of the tooth template 7, the use of bounding boxes is not necessarily required.

Figure 3:
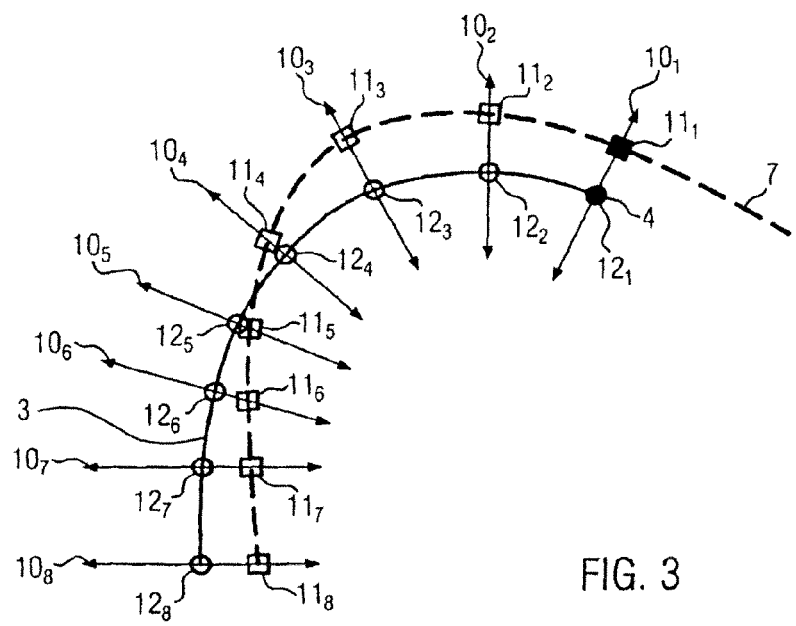
FIG. 3 shows rays to select handles and targets.

For deforming the tooth template 7 such that the cavity in the rest tooth 1 may be covered by a suitable part of the tooth template 7, an algorithm may be used, wherein as shown in FIG. 3, lines $10_1$-$10_8$ are cast each going through a point on the surface of the rest tooth, each of the lines being directed along the normal direction of the point of the surface of the rest tooth. The lines may be cast starting at points on the outer surface 3 of the rest tooth 1 or starting at points on the preparation margin 4.

If an intersection of a line $10_1$-$10_8$ with the tooth template 7 is observed the respective intersection point on the template 7 may be chosen as handle $11_1$-$11_8$ (squares) and the respective point on the rest tooth 1 as respective target $12_1$-$12_8$ (circles). If an intersection of a line $10_1$-$10_8$ with the tooth template 7 is observed in both positive and negative normal directions, the intersection point with the smaller distance to the point the line going through of the surface of the rest tooth 1 may be chosen.

The open circles $12_2$-$12_8$ correspond to targets on the outer surface 3 of the rest tooth 1 having respective handles on the tooth template 7 indicated by the open squares $11_2$-$11_8$. The filled circle $12_1$ corresponds to a point on the preparation margin 4 and the respective handle on the tooth template 7 is indicated by the filled square $11_1$.

After having determined the handles $11_1$-$11_8$ on the tooth template 7 and respective targets $12_1$-$12_8$ on the rest tooth 1, the deformation of the tooth template 7 may be performed as an iterative process.

The deformation of the tooth template 7, according to the targets $12_1$-$12_8$ may be performed in the unprepared region of the rest tooth 1 and at the preparation margin 4. As the algorithm starts at points on the surface of the rest tooth 1 and the algorithm uses these points as targets $12_1$-$12_8$, it is not required to make a determination after each iteration step whether a point of the tooth template 7 which may be a handle for the next iteration step lies above the prepared or the unprepared region of the rest tooth 1 or above the preparation margin 4. The algorithm may be considered to deform the tooth template 7 by pulling the tooth template 7 towards the rest tooth 1 and as the location of the targets 12₁-12₈ on the rest tooth 1 is known, it is also known that a handle on the tooth template 7 will be deformed towards this location.

In the article of T. Steinbrecher et al., the deformation vectors are determined starting from vertices on the model tooth and thus after each iteration step a new classification of the hits on the surface of the rest tooth has to be performed.

Figure 4A:
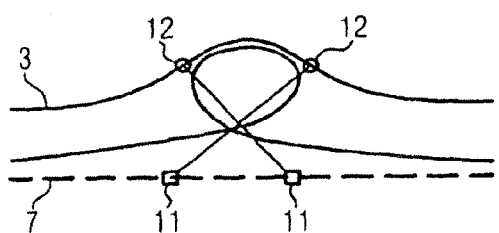
FIG. 4a shows the result of a surface deformation in a single step.
Figure 4B:
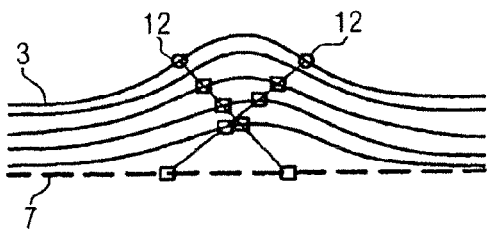
FIG. 4b shows the result of a surface deformation using an iterative process with successively increasing handle weights.
Figure 5:
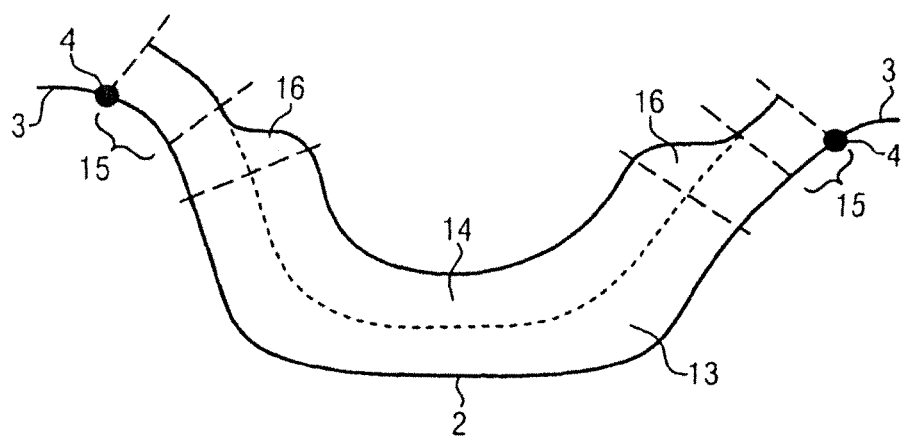
FIG. 5 shows cement gap and spacer gap.

Handle weights may increase form low values to bigger values successively during the iterative process. FIGS. 4a and 4b illustratively show the result when performing the deformation in a single step and when performing the deformation using an iterative process, respectively. When using a single step for performing the deformation, self-intersections may be produced resulting in a deformed surface that is not usable for a dental restoration. However, when the iteration starts with low handle weights, the shape preservation characteristic of the Laplacian surface deformation is predominant and self-intersection is avoided. As shown in FIG. 4b the deformed tooth template 7 is adjusted to fit the outer surface 3.

Once new handles are selected, the new deformed shape of the tooth template has to be calculated. This may be achieved by solving an optimization problem, wherein a global deformation energy E may be constructed that measures how much a deformed triangle mesh with vertex coordinates $p_1', \ldots, p_n'$ differs from its initial rest pose with vertex coordinates $p_1, \ldots, p_n$. The deformation energy E integrates locally defined changes of the shape. The local shape of vertex i is described by the discrete Laplacian $\Delta p = 2H_i n_i$ which is a three dimensional vector that points in the direction of the unit length vertex normal $n_i$ and has a magnitude twice the mean curvature $H_i$.

The global deformation energy may be formulated as $$E(p_1', \ldots p_n') = \sum_i A_i \|\delta_i' - \delta_i\|^2 + \sum_j w_j \|h_j' - h_j\|^2, \quad (1)$$

wherein the left term measures the weighted squared distance between local shapes in the deformed mesh and local shapes in the rest pose. The right term of equation 1 measures the weighted squared distance between the positions of the deformed handles $h_j' = h_j(p_1', \ldots, p_n')$ and their targets $h_j = h_j(p_1, \ldots, p_n)$. $A_i$ is the two dimensional Voronoi area around the vertex I and $w_j = 1$.

The discrete Laplacian may be computed as $$\delta_i = \frac{1}{2 \cdot A_i} \cdot \sum (\cot \alpha_{ij} + \cot \beta_{ij}) \cdot (p_i - p_j), \quad (2)$$

wherein vertices j are the one-ring neighbours of vertex i and $\alpha_{ij}$ and $\beta_{ij}$ are the two angles opposite to the edge (i,j). In the presence of obtuse triangles, the respective Voronoi region extends beyond the one-ring neighbours of the vertex. To guarantee a perfect tiling of the surface without overlapping the Voronoi area is truncated, resulting in the Laplacian of a deformed vertex being:

$$\delta_i' = \frac{1}{2 \cdot A_i'} \cdot \sum (\cot \alpha_{ij}' + \cot \beta_{ij}') \cdot (p_i' - p_j'). \quad (3)$$

The handles j are allowed to be at any point of the triangle surface (and not only being vertices) by using barycentric coordinates $(\lambda_{j1}, \lambda_{j2}, \lambda_{j3})$ of the respective triangle $(p_{j1}, p_{j2}, p_{j3})$:

$$h_j(p_1, \ldots, p_n) = \lambda_{j1} p_{j1} + \lambda_{j2} p_{j2} + \lambda_{j3} p_{j3}, \quad (4)$$

where $$\lambda_{jk} = \frac{\|(p_{ja} - h_j) \times (p_{jb} - h_j)\|}{\|(p_{j2} - p_{j1}) \times (p_{j3} - p_{j1})\|} \quad (5)$$

for a≠b, a≠k and b≠k.

It is assumed that areas and angles are preserved such that $\alpha_{ij}' = \alpha_{ij}$, $\beta_{ij}' = \beta_{ij}$ and $A_i' = A_i$ and hence, the Laplacian operator $\Delta p_i'$ can be described linearly in the deformed vertex coordinates. Thus, the global deformation energy E has a quadratic form $$E(p') = \|\sqrt{M}(Lp' - \delta)\|^2 + \|\sqrt{W}(Cp' - h)\|^2, \quad (6)$$

is where L is the matrix form of the Laplacian operator, C encapsulates the barycentric coordinates, $\delta$ is a vector with the x, y or z coordinates of Laplacian $\delta_i$, h is a vector containing the respective handle coordinates, M and W are diagonal matrices containing the weights $A_i$ and $w_j$, respectively, and p' is the vector with the deformed vertex coordinates. The deformed tooth template can be reconstructed by a minimization in the linear least square sense.

The global deformation energy can be reformulated to:

$$E(p') = p'^T(L^T ML + C^T WC)p' - 2p'^T(L^T M\delta + C^T Wh) + \delta^T M\delta + h^T Wh. \quad (7)$$

The minimization $$\frac{\partial}{\partial p'} E(p') = 0 \quad (8)$$

leads to the normal equations $$(L^T ML + C^T WC)p' = L^T M\delta + C^T Wh \quad (9)$$

which are basically a linear system of size n×n.

For the Laplacian surface deformation of the tooth template 7 the handleweights $handlew_{g,I,p,D}$ (i, d, α) may be defined by the following formula:

$$handlew_{g,I,p,D}(i, d, \alpha) = globalw_{g,I,p}(i) \cdot distw(i, d)_{D,I} \cdot anglew(\alpha). \quad (10)$$

$$globalw_{g,I,p}(i) = g \cdot \left(\frac{i}{I}\right)^p, \quad (11)$$

wherein g≥1 is a global weighting factor, I≥1 is the number of iteration steps, i≥1 is the current iteration step and the power p≥1 determines the shape of the function.

The distance weighting function may be defined by $$distw(i, d)_{D,I} = 1 - wendland_{4,I}(I - i) + \begin{cases} 0 & \text{for } d \geq D \\ wendland_{4,I}(I - i) \cdot wendland_{4,D}(d) & \text{else,} \end{cases} \quad (12a)$$

or preferably by $$distw(i, d)_{D,i} = \quad (12b)$$

$$wendland_{8,I}(i) + \begin{cases} 0 & \text{for } d \geq D \\ (1 - wendland_{8,I}(i)) \cdot wendland_{4,D}(d) & \text{else,} \end{cases}$$

wherein d≥0 is the distance, D≥0 is the support.

The Wendland weighting function is defined by $$wendland_{p,r}(x) = \left(1 - \frac{x}{r}\right)^p \cdot \left(\frac{p \cdot x}{r} + 1\right) \quad (13)$$

wherein r≥0 is the radius of support and p≥2 determines the shape of the function.

The angleweight is defined by the following formula:

$$anglew(\alpha) = \begin{cases} 0 & \text{for } \alpha \geq \pi/2 \\ wendland_{4,\pi/2}(a) & \text{else,} \end{cases} \quad (14)$$

wherein α∈[0,π] is the angle between the normal direction of the target and the normal direction of the handle.

After applying a fixed number of iterations i a tooth template 7 may exist that has been deformed such that it describes the unprepared regions of the rest tooth 1. This part of the tooth template 7 that lies inside the preparation margin 4 may describe the surface of the dental restoration to be designed, wherein this surface represents the surface of the dental restoration that will not be hidden by the rest tooth after attaching the dental restoration to the rest tooth 1. This surface may be e.g. a part of the chewing surface of a molar.

For the final design of the dental restoration the part of the tooth template 7 inside the preparation margin is relevant. To extract this part, the so-called deformed tooth template 18, from the tooth template 7, a virtual cut along the preparation margin 4 may be performed, such that only data being related to the tooth template 7 inside of the preparation margin is taken into account for further processes.

After finalizing the deformation of the tooth template 7, the surface of the dental restoration describing the lower surface 2 may be adapted by adding a cement gap 13 and a spacer gap 14, wherein a at some distance 15 from the preparation margin 4 a spacer transition 16 may exist. For example, an offset function may be chosen to achieve a smooth transition from the cement gap 13 to the spacer gap 14:

$$offset_{b,t,c,s}(d) = c + \begin{cases} 0 & \text{for } d \leq b \\ s & \text{for } d \geq b + t \\ \frac{s}{2} \cdot \left(1 + \sin\left(\pi \cdot \frac{d-b}{t} - \frac{\pi}{2}\right)\right) & \text{else,} \end{cases} \quad (15)$$

wherein d is the geodesic distance to the preparation margin 4, b is the distance of the spacer gap 14 to the preparation margin 4, t is the spacer gap transition 16, c is the thickness of the cement gap 13 and s is the thickness of the spacer gap 14.

Figure 6:
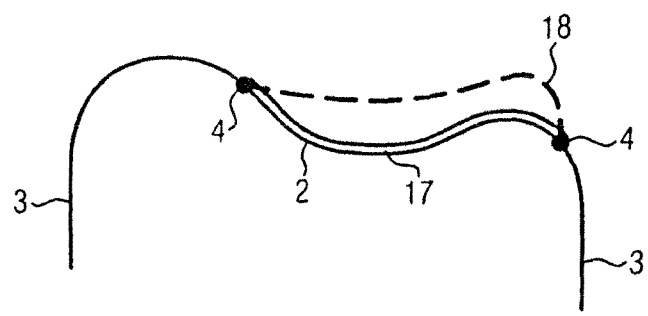
FIG. 6 shows prepared tooth, deformed tooth template and minimal surface.
Figure 7A:
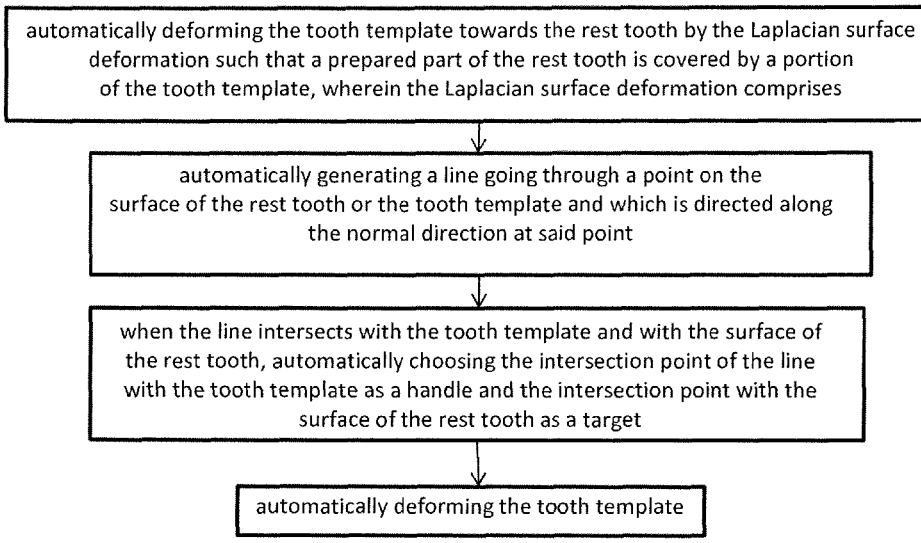
FIG. 7A is a flow chart of a method according to one embodiment of the invention.
Figure 7B:
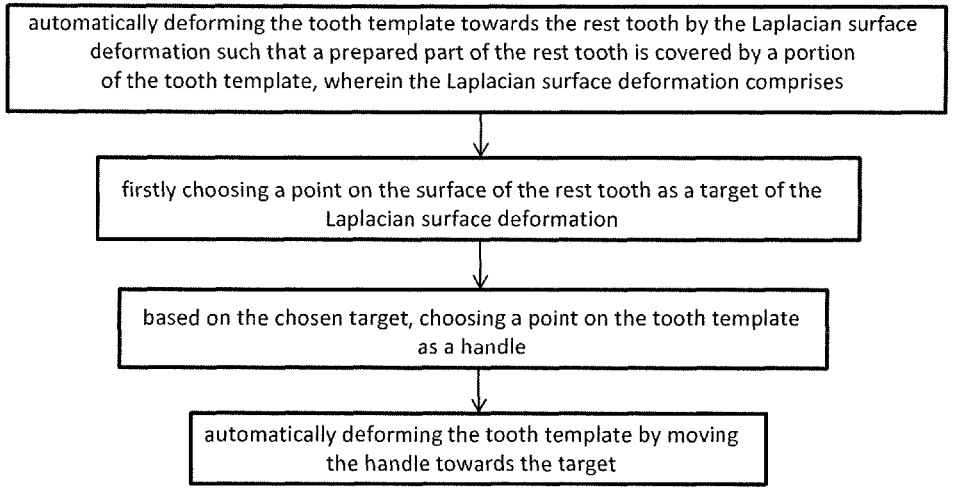
FIG. 7B is a flow chart of a method according to another embodiment of the invention.

For the manufacturing of the dental restoration it is required that a certain minimum wall thickness is ensured. Therefore, a minimal surface 17, as shown in FIG. 6, may be constructed and every vertex of the deformed tooth template 18 may be required to lie above this minimal surface 17. The minimal surface 17 may be constructed by an offset on the rest tooth 1 and the mesh of the cavity to be provided with the dental restoration.

To correct the deformed tooth template 18 with respect to the minimal surface 17, rays (i.e. lines) may be cast from vertices of the deformed tooth template 18 along the positive normal direction of the respective vertex. A vertex is below the minimum wall thickness if the ray belonging to said vertex intersects a mesh triangle of the minimal surface and the difference between the normal direction of the vertex and the normal direction of the triangle is less than π/2. In such a case, a respective handle is selected and the intersection point on the minimum surface 17 is selected as target. Handle weights may be set in the same manner as for the deformation process of the tooth template 7, but the distance weighting is described independent from the current iteration as no general positioning is required.

In order to achieve a good correction result, first the deformation may be applied to the boundary of the deformed tooth template 18 while fixing handles in the interior using large handle weights. In a second deformation step, the boundary may be fixed and the interior may be adjusted to the minimal surface 17.

One exemplary for an offset to define the minimal surface is given by $$o_{b,w,W}(d) = \begin{cases} 0 & \text{for } d \leq 0 \\ b\sqrt{1 - \left(1 - \frac{d}{b}\right)^2} & \text{for } d > 0, d \leq b \\ w & \text{for } d \geq W \\ b + \frac{w-b}{2} \cdot \left(1 + \sin\left(\pi \cdot \frac{d-b}{W-b} - \frac{\pi}{2}\right)\right) & \text{else,} \end{cases} \quad (16)$$

wherein b>0 is a predefined wall thickness at the boundary and w>b a predefined wall thickness at a geodesic distance W>b from the boundary. This function guarantees a minimum wall thickness b at the boundary and ensures that deformed tooth template 18 forms at least almost a rectangular angle at the preparation margin 4 with respect to the lower surface 2 of rest tooth 1.

Depending on the shape of the transition between the lower surface 2 and the unprepared part of the rest tooth 1, the thickening near the preparation margin 4 may have different forms. In case, the transition forms almost a rectangular angle, then almost no or none thickening can be observed and a flat and smooth transition between the corrected, deformed tooth template (i.e. the deformed tooth template 18 that has been corrected taking into account a minimal thickness) and the unprepared part of the rest tooth 1 is provided. In case, the transition has an angle smaller than 90°, then a thickening may be provided ensuring that the dental restoration will have a sufficient thickness also near the preparation margin.

Another possibility for defining a minimal surface 17 is to apply an offset along the normal direction of each vertex of the lower surface 2 (wherein preferably the cement gap 13 and/or spacer gap 14 has already been added to the lower surface 2). Such an offset may have a predefined value over the whole range of the lower surface 2 or the to offset may have smaller values near the preparation margin 4 and larger values at some predefined distance from the preparation margin 4 or vice versa. Instead of taking into account the normal direction of each vertex, an average of several normal directions of several vertices may be determined and then an offset may be applied to this averaged normal direction.

The invention claimed is:

1. Computer-implemented method for digitally designing a dental restoration for a rest tooth using a tooth template and a Laplacian surface deformation, wherein the rest tooth is described by scanned data of the rest tooth or a dental model of the rest tooth, the tooth template is described by data of the tooth template, and wherein a normal direction to a surface at a point is the same as a normal direction to a tangent plane to the surface at the point, the method comprising the steps of:

generating, in a processor, for display on a computer display, data sets for the rest tooth and tooth template depicted as objects;

automatically deforming, via the processor, the tooth template towards the rest tooth by the Laplacian surface deformation such that a prepared part of the rest tooth, within a preparation margin, is covered by a portion of the tooth template;

wherein the Laplacian surface deformation comprises:

automatically generating a line going through a point on the surface of the rest tooth or the tooth template and which is directed along the normal direction to the surface at said point;

when the line intersects with the tooth template and with the surface of the rest tooth, automatically choosing the intersection point of the line with the tooth template as a handle and the intersection point with the surface of the rest tooth as a target; and automatically deforming the tooth template;

wherein the data of the tooth template comprises a mesh of polygons describing the surface of the tooth template, and wherein the Laplacian surface deformation further comprises using a handle that lies inside a polygon of the mesh of the tooth template.

2. The computer-implemented method according to claim 1, wherein automatically deforming the tooth template in the Laplacian surface deformation further comprises moving the handle towards the target.

3. The computer-implemented method according to claim 1, wherein the Laplacian surface deformation further comprises automatically iteratively performing the deformation of the tooth template.

4. The computer-implemented method according to claim 3, wherein automatically iteratively performing the deformation of the tooth template uses a handle weight that is increased as the iteration process proceeds.

5. The computer-implemented method according to claim 4, wherein the method further comprises the step of defining the handle weight for the deformation as a product comprising a global weight increasing with each iteration step and at least one or two of:

a distance weight decreasing with increasing distances between the target and the handle, wherein the dependence of the distance weight on the distance may vary with each iteration step; or an angle weight that depends on the angle between the normal direction of the target and the normal direction of the handle.

6. The computer-implemented method according to claim 3, wherein the method further comprises the step of automatically extracting a portion of the tooth template by digitally cutting the deformed tooth template along a preparation margin.

7. The computer-implemented method according to claim 6, wherein the method further comprises the step of automatically combining data representing the cut out deformed tooth template portion with data representing the surface of the rest tooth inside the preparation margin to provide data of a three-dimensional design of the dental restoration.

8. The computer-implemented method according to claim 7, wherein the method further comprises the step of automatically adding a cement gap and/or a spacer gap to the data representing the surface of the dental restoration that would be in contact with the rest tooth, the so-called lower surface.

9. The computer-implemented method according to claim 8, wherein the adding is performed by automatically applying an offset along the normal directions of points, of the lower surface.

10. The computer-implemented method according to claim 1, wherein the method further comprises the step of automatically positioning the tooth template with respect to rest tooth by aligning the rest tooth and the tooth template to coincide in buccal direction and in occlusal direction.

11. The computer-implemented method according to claim 10, wherein the method further comprises the step of automatically scaling the tooth template in buccal and in direction of the mesial-distal axis according to the horizontal extent of the prepared part of the rest tooth.

12. The computer-implemented method according to claim 4, including starting with a pre-defined minimum handle weight.

13. The computer-implemented method according to claim 9, wherein the points are vertices.

14. The computer-implemented method according to claim 11, wherein no scaling in occlusal direction is performed.

15. The computer-implemented method according to claim 1, wherein the point on the surface of the tooth template is a vertex or a point inside a triangle of a polygonal mesh that describes the surface of the tooth template and wherein the normal direction at a vertex is defined by the average of normal directions of triangles that have the vertex as a corner point or of triangles that lie within a sphere or volume of a predefined size around the vertex.

16. A non-transitory computer-readable medium having stored thereon instructions, which when executed by a processor, performs a method for digitally designing a dental restoration for a rest tooth using a tooth template and a Laplacian surface deformation, wherein the rest tooth is described by scanned data of the rest tooth or a dental model of the rest tooth, the tooth template is described by data of the tooth template, and wherein a normal direction to a surface at a point is the same as a normal direction to a tangent plane to the surface at the point, the method comprising the steps of:

generating, in a processor, for display on a computer display, data sets for the rest tooth and tooth template depicted as objects;

automatically deforming, via the processor, the tooth template towards the rest tooth by the Laplacian surface deformation such that a prepared part of the rest tooth, within a preparation margin, is covered by a portion of the tooth template;

wherein the Laplacian surface deformation comprises:

automatically generating a line going through a point on the surface of the rest tooth or the tooth template and which is directed along the normal direction to the surface at said point;

when the line intersects with the tooth template and with the surface of the rest tooth, automatically choosing the intersection point of the line with the tooth template as a handle and the intersection point with the surface of the rest tooth as a target; and automatically deforming the tooth template; and wherein the data of the tooth template comprises a mesh of polygons describing the surface of the tooth template, and wherein the Laplacian surface deformation further comprises using a handle that lies inside a polygon of the mesh of the tooth template.

17. Computer-implemented method for digitally designing a dental restoration for a rest tooth using a tooth template and a Laplacian surface deformation, wherein the rest tooth is described by scanned data of the rest tooth or a dental model of the rest tooth, the tooth template is described by data of the tooth template and the data of the tooth template comprises a mesh of polygons describing a surface of the tooth template, and wherein the Laplacian surface deformation comprises using a handle that lies inside a polygon of the mesh of the tooth template, and wherein a normal direction to a surface at a point is the same as a normal direction to a tangent plane to the surface at the point, the method comprising the steps of:

generating, in a processor, for display on a computer display, data sets for the rest tooth and tooth template depicted as objects;

automatically deforming, via the processor, the tooth template towards the rest tooth by the Laplacian surface deformation such that a prepared part of the rest tooth, within a preparation margin, is covered by a portion of the tooth template;

wherein firstly a point on the surface of the rest tooth is chosen as a target of the Laplacian surface deformation and then based on the chosen target a point on the tooth template is chosen as a handle, and, automatically deforming the tooth template by moving the handle towards the target.

\* \* \* \* \*